(12) United States Patent
Stahl et al.

(10) Patent No.: US 9,811,051 B2
(45) Date of Patent: Nov. 7, 2017

(54) APPARATUS AND METHOD FOR PERFORMING IN-LINE LENS-FREE DIGITAL HOLOGRAPHY OF AN OBJECT

(71) Applicant: IMEC VZW, Leuven (BE)

(72) Inventors: Richard Stahl, Rotselaar (BE); Murali Jayapala, Boutersem (BE); Andy Lambrechts, Herent (BE); Geert Vanmeerbeeck, Keerbergen (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/039,549

(22) PCT Filed: Dec. 2, 2014

(86) PCT No.: PCT/EP2014/076270
§ 371 (c)(1),
(2) Date: May 26, 2016

(87) PCT Pub. No.: WO2015/082476
PCT Pub. Date: Jun. 11, 2015

(65) Prior Publication Data
US 2017/0031318 A1    Feb. 2, 2017

(30) Foreign Application Priority Data
Dec. 2, 2013   (EP) .................................... 13195248

(51) Int. Cl.
*G03H 1/04*    (2006.01)
*H04N 9/04*    (2006.01)
(Continued)

(52) U.S. Cl.
CPC ......... *G03H 1/0443* (2013.01); *G01N 15/147* (2013.01); *G01N 15/1429* (2013.01);
(Continued)

(58) Field of Classification Search
CPC ............. G01B 9/02047; G03H 1/0443; G03H 1/0465; G03H 1/0493; G03H 2001/0452
(Continued)

(56) References Cited

U.S. PATENT DOCUMENTS

| 6,411,406 B1 * | 6/2002 | Kreuzer | G01N 23/20 359/1 |
| 2010/0253986 A1 | 10/2010 | Awatsuji et al. | |
| 2011/0292402 A1 * | 12/2011 | Awatsuji | G01B 9/021 356/495 |

FOREIGN PATENT DOCUMENTS

WO    2012/150472 A1    11/2012

OTHER PUBLICATIONS

Fienup, J.R., "Reconstruction of an Object From the Modulus of its Fourier Transform", Optics Letters, vol. 3, No. 1, Jul. 1978, pp. 27-29.
(Continued)

*Primary Examiner* — Jonathan Hansen
(74) *Attorney, Agent, or Firm* — McDonnell Boehnen Hulbert & Berghoff LLP (57) ABSTRACT

The present disclosure relates to apparatuses and methods for performing in-line lens-free digital holography of objects. At least one embodiment relates to an apparatus for performing in-line lens-free digital holography of an object. The apparatus includes a point light source adapted for emitting coherent light. The apparatus also includes an image sensing device adapted and arranged for recording interference patterns resulting from interference from light waves directly originating from the point light source and object light waves. The object light waves originate from light waves from the point light source that are scattered or reflected by the object. The image sensing device comprises a plurality of pixels. The point light source comprises a broad wavelength spectrum light source and a pinhole
(Continued)

structure. The image sensing device comprises a respective narrow band wavelength filter positioned above each pixel that filters within a broad wavelength spectrum of the point light source.

20 Claims, 8 Drawing Sheets (51) Int. Cl.
H04N 5/33 (2006.01)
G01N 15/14 (2006.01)
G03H 1/08 (2006.01)
G03H 1/02 (2006.01)
G03H 1/26 (2006.01)

(52) U.S. Cl.
CPC ....... *G01N 15/1434* (2013.01); *G03H 1/0404* (2013.01); *G03H 1/0465* (2013.01); *G03H 1/0486* (2013.01); *G03H 1/0493* (2013.01); *H04N 5/332* (2013.01); *H04N 9/045* (2013.01); *G01N 2015/1454* (2013.01); *G03H 1/0866* (2013.01); *G03H 2001/0212* (2013.01); *G03H 2001/0428* (2013.01); *G03H 2001/0447* (2013.01); *G03H 2001/0452* (2013.01); *G03H 2001/0497* (2013.01); *G03H 2001/266* (2013.01); *G03H 2210/12* (2013.01); *G03H 2210/13* (2013.01); *G03H 2226/11* (2013.01); *G03H 2240/62* (2013.01)

(58) Field of Classification Search
USPC .......................................................... 356/457
See application file for complete search history.

(56) References Cited

OTHER PUBLICATIONS

Fienup, J.R.,"Phase Retrieval Algorithms: A Comparison", Applied Optics, vol. 21, No. 15, Aug. 1, 1982, pp. 2758-2769.
Awatsuji, Yasuhiro et al., "Single-Shot Phase-Shifting Color Digital Holography", Lasers and Electro-Optics Society, The 20th Annual Meeting of the IEEE, Oct. 1, 2007, pp. 84-85.
Kakue, Takashi et al., "Parallel Phase-Shifting Color Digital Holography Using Two Phase Shifts", Appiled Optics, vol. 48, No. 34, Dec. 1, 2009, pp. H244-H250.
Garcia-Sucerquia, Jorge, "Color Lensless Digital Holographic Microscopy With Micrometer Resolution", Optics Letters, vol. 37, No. 10, May 15, 2012, pp. 1724-1726.
Greenbaum, Alon et al., "Wide-Field Computational Color Imaging Using Pixel Super-Resolved On-Chip Microscopy", Optics Express, vol. 21, No. 10, May 14, 2013, pp. 12469-12483.
European Search Report, European Patent Application No. 13195248.3, dated Apr. 24, 2014, 11 pages.
PCT Search Report and Written Opinion, PCT International Application No. PCT/EP2014/076270, dated Feb. 9, 2015, 16 pages.
Gorocs, Zoltan et al., "In-Line Color Digital Holographic Microscope for Water Quality Measurements", Laser Applications in Life Sciences, SPIE, vol. 7376, No. 1, Jun. 25, 2010, pp. 1-10.

* cited by examiner

APPARATUS AND METHOD FOR PERFORMING IN-LINE LENS-FREE DIGITAL HOLOGRAPHY OF AN OBJECT

CROSS-REFERENCE TO RELATED APPLICATION

The present application is a national stage entry of PCT/EP2014/076270 filed Dec. 2, 2014, which claims priority to European Patent Application No. 13195248.3 filed on Dec. 2, 2013, the contents of each of which are hereby incorporated by reference.

TECHNICAL FIELD

The present disclosure relates to an apparatus and method for performing in-line lens-free digital holography of an object.

BACKGROUND ART

Gabor invented holography in 1948. It involves irradiating an object with a radiation beam of strong coherence. The waves which are scattered by the object interfere with the background wave on a photographic film or digital image sensor, where interference patterns are recorded. Based on the recorded interference pattern it is possible to reconstruct the original object wave field.

Since digital image sensors (camera sensors organized into semiconductor matrix based for instance on CCD, CMOS and similar configurations), digital holography has gained grounds. Holograms exposed on conventional photo materials need to be treated physically or chemically. This need is removed in the field of digital holograms. Moreover, the recorded hologram information can be stored in digital memory. The stored hologram can also be improved by appropriate software algorithms on the basis of the digital information only. The spatial image can for instance also be reconstructed from the hologram in a numerical way; there is no need for an illuminating light source and other optical means for the reconstruction of the spatial image.

As is known to the skilled person, lens free imaging is basically a microscopic imaging method based on the principal of in-line holography. In-line holography is a commonly used holographic imaging technique, and is known because of its simplicity and minimal optical hardware requirements. The in-line holography technique however suffers from the so-called twin-image problem, being the inherent artifact of out-of-focus virtual object information appearing in the in-focus real object image. Techniques are known to the skilled person that can eliminate the twin-image artifact. They can be categorized in two groups. A first group is constituted by support-/mask-based methods, which cannot be applied in complex object imaging as it is impossible to create a good mask for an object without obscuring the object right next to it. The other group is constituted of mask less iterative phase retrieval methods, which rely on acquisition of multiple images with varying information content. These multiple images with varying information content can be acquired by varying the phase, the imaging distance or the illumination wavelength between the different subsequent acquisitions. The multi-image acquisition can either performed in the time domain, for instance sequentially recording image after image, or in the space domain, for instance splitting up the light into multiple optical parts to vary the phase of light arriving at the sensor (at the pixel level) or to vary the optical path (at sensor level).

The multi-image acquisition performed in the time domain is not suitable for high speed imaging (e.g. in real-time video applications) as the acquisitions at different time-instances will typically record slightly or seriously different object perspectives (for instance objects rotating or shifting). The multi-image acquisition performed in the spatial domain, realized in the prior art for example using a beam splitter, has limited performance due to the fact that the imaging conditions cannot be optimized due to the presence of the extra optical hardware. For instance, a beam splitter does itself restrict the minimal distance from object to imager. This results in serious resolution degradation of the final reconstructed image.

Today, there exists a need for apparatuses and methods which are suitable for performing high-speed high resolution in-line lens free digital imaging.

In WO2012/150472 an apparatus for producing three-dimensional color images is disclosed, the apparatus comprising at least two feeding light sources generating coherent light beams of different colors, at least two optical fibers having input ends and light emitting ends, the input ends of the optical fibers being connected to the feeding light sources, respectively, the light emitting ends of the optical fibers being placed closely side by side and constituting an illuminating light source, an object space suitable for locating an object to be illuminated by the illuminating light source, at least one digital image sensing device for recording an interference pattern of reference light beams and object light beams scattered on or reflected by the object as a hologram, and the digital image processing device for producing the three dimensional color images of the object from the hologram recorded by the at least one digital image sensing device with a correction of distortions resulting from placing side by side the light emitting ends of the optical fibers.

Here, a plurality of feeding light sources each emit light with a very narrow wavelength spectrum, from neighboring but still substantially different locations, such that a correction of distortions is necessary. Such a configuration puts stringent conditions on the light sources used, making it an expensive solution. Moreover, multiple sources are needed, which again increases the cost and results in relatively large devices. Also, at the digital image sensing device, wavelength filters with a relatively broad wavelength range are applied, in order to be able to extract information for different colors.

SUMMARY OF THE DISCLOSURE

It is an aim of the present disclosure to provide an apparatus for performing in-line lens-free digital holography of an object which is suitable for performing high-speed high resolution holographic imaging.

This aim is achieved according to the disclosure with the apparatus showing the technical characteristics of the first independent claim.

It is another aim of the present disclosure to provide a method for performing in-line lens-free digital holography of an object.

This aim is achieved according to the disclosure with a method comprising the steps of the second independent claim.

In a first aspect of the present disclosure, an apparatus is disclosed for performing in-line lens-free digital holography of an object, comprising:
- a single point light source adapted for emitting coherent light;
- an image sensing device adapted and arranged for recording interference patterns resulting from interference from light waves directly originating from the point light source and object light waves, the object light waves originating from scattering or reflection of light waves from the point light source by the object, the image sensing device comprising a plurality of pixels;
- wherein the image sensing device is adapted for receiving and recording, at the same moment in time, a plurality of interference patterns by a respective plurality of disjoint subsets of pixels.

The skilled person will recognise that, inherently, the plurality of interference patterns is suitable for retrieving or deriving phase information of the three-dimensional interference space, more specifically suitable for retrieving or deriving phase information of the object.

According to preferred embodiments, the object is a translucent object. More preferably, the object can be transparent. According to preferred embodiments the object can be more than 10% or more than 25%, or more than 50% or more than 60% or more than 70% or more than 80% or more than 90% or more than 95% or more than 99% translucent or transparent, which means that it would allow a respective percentage of the incoming light passing through it.

A single point light source is a light source of the point source type. Although the concept of a point source is in principle a mathematical concept, a light source of the point source type is meant to be any light source which approximates the mathematical concept to a very large extent, as will be recognised by the skilled person. It may for instance be a light source with an emission aperture of 1 micrometer to 100 micrometer. For example, the aperture size can be 1 micrometer, which would be considered "small". For example, the aperture size can be 50 micrometer, this would be considered "large".

According to preferred embodiments, the apparatus further comprises or relates to an object space suitable for locating the object and positioned in close proximity of the point light source, for subjecting the object to light waves of the point light source. The object can be positioned within the range of hundred or a few hundreds (e.g. 200 or 300) of micrometers to a ten or a few tens (e.g. 20 or 30) of centimeters from the light source. For example, the object can be positioned at a distance of 1 millimeter from the light source.

The object space is preferably situated in between the point light source and the image sensing device. The object space is preferably situated along or within the light path of the light emitted from the point light source and the image sensing device.

According to preferred embodiments, the image sensing device is a digital image sensing device. The digital image sensing device may comprise a plurality of pixels. A pixel can comprise or consist of a photodiode and readout electronics.

According to preferred embodiments, the apparatus further comprises a processing means adapted for deriving phase information by using at least the plurality of interference patterns, or based on the plurality of interference patterns, or based on the plurality of interference patterns only. Deriving or retrieving phase information based on the plurality of interference patterns may comprise an up-sampling step of the holographic images, to increase the resolution of the image. It has moreover been shown that the use of state of the art up-sampling methods which can be used to increase the resolution of each of the recorded interference patterns does not impact the convergence of typical iterative phase retrieval methods.

According to preferred embodiments, the pixels are arranged in a regularly spaced matrix pattern.

According to preferred embodiments, pixels of each subset of pixels are homogeneously distributed over a main planar surface of the image sensing device.

According to preferred embodiments, pixels of each subset of pixels are spaced from each other at constant distances, and wherein respective resulting grids are offset with respect to each other by constant distances.

For instance, in the case of two subsets of pixels, these can be organized in a chess board configuration.

According to preferred embodiments, the pixels of each disjoint subset are arranged in rows (or columns) of the regularly spaced matrix pattern.

According to preferred embodiments, the point light source comprises a broad wavelength spectrum light source and a pinhole structure, the broad wavelength spectrum light source being arranged such that it emits light towards a pinhole structure. In another view, the point light source, preferably a broad wavelength spectrum light source, can be embodied as a light source behind, i.e. on a first side of, a pinhole in a plate or other light blocking means. The other side of the plate of light blocking means can host the object space and/or image sensing device.

According to preferred embodiments, the broad wavelength spectrum light source comprises a white laser device or a LED device.

According to preferred embodiments, the image sensing device comprises for each of the disjoint subsets of pixels, a respective narrow band wavelength filter positioned above each of the pixels of the disjoint subset of pixels, wherein a wavelength range of each narrow band wavelength filter falls within the broad wavelength spectrum of the point light source, and wherein these wavelength ranges of the narrow band wavelength filters are non-overlapping. In other words, preferably, the passbands of different filters do not overlap. The skilled person will understand that, in practice, this means that the overlap is below a predetermined level. For a given application, the skilled person is able to determine a suitable degree of overlap. For instance, a first narrow band wavelength filter can be considered as overlapping with a second narrow band wavelength filter if there exists more than 90, or more than 95, or more than 98, or more than 99, or more than 99.9 percent overlap. In other words, a first narrow band wavelength filter can be considered as non-overlapping with a second narrow band wavelength filter if there exists less than 10, or less than 5, or less than 2, or less than 1, or less than 0.01 percent overlap.

According to preferred embodiments, the wavelength range of each narrow band filter is smaller than N nm, and wherein the broad wavelength spectrum has a wavelength range larger than N×M nm, M being the number of narrow band filter comprised or present in the apparatus.

For example, in case of four wavelength filters, which is a preferred embodiment, the wavelength range of each narrow band filter can for instance be smaller than 5 nm (for instance within the range of 1 nm to 5 nm; smaller values are not excluded but may require light sources with relatively high intensity; the latter may be detrimental to certain objects, as for instance biological objects), and the broad wavelength spectrum can have a wavelength range larger than 20 nm (for instance the wavelength range can be within the range between 20 nm and 100 nm). In another example, the wavelength range of each narrow band filter of a set of ten non-overlapping narrow band wavelength filters can be smaller than 2 nm, and all of them can be fit in a 20 nm broad wavelength spectrum. More generally, the sum of the wavelength ranges of the respective set of narrow band filters is preferably smaller than the wavelength range of the broad wavelength spectrum. The skilled person will recognize that a broad wavelength spectrum comprises a spectrum which is continuous and extends over a broad wavelength range. It is a characteristic of such broad wavelength spectrum that the light intensity within this broad range is never close to zero or zero, i.e. the intensity of the broad spectrum wavelength light source is always substantially different from zero, within this broad range. According to preferred embodiments, the broad wavelength spectrum has a Gaussian-type profile.

In a second aspect of the present disclosure, a method is disclosed for performing in-line lens-free digital holography of an object, comprising:

emitting essentially coherent light from a single point light source;

locating the object, for instance in an object space, positioned in close proximity of the point light source, and subjecting the object to light waves of the point light source;

receiving and recording interference patterns resulting from interference from light waves directly originating from the point light source and object light waves, the object light waves originating from scattering or reflection of light waves from the point light source by the object, with an image sensing device comprising a plurality of pixels;

wherein receiving and recording interference patterns comprises receiving and recording at the same moment in time a plurality of interference patterns by a respective plurality of disjoint subsets of pixels.

According to preferred embodiments, the method further comprises retrieving or deriving phase information of the object by performing an iterative phase retrieval algorithm, using the plurality of interference patterns, for instance performed on a processing means. Iterative phase retrieval algorithms are known to the skilled person. This field has been explored scientifically since the 1970's. See for instance J. R. Fienup, "Reconstruction of an object from the modulus of its Fourier transform", Optics Letters, Vol. 3, Issue 1, pp. 27-29 (1978) and J. R. Fienup, "Phase retrieval algorithms: a comparison", Applied Optics, Vol. 21, Issue 15, pp. 2758-2769 (1982).

According to preferred embodiments, the method further comprises emitting a broad wavelength spectrum of light with the point light source and filtering the incoming light for each of the pixels belonging to a same subset, with a respective narrow band wavelength filter, for each disjoint subset, before receiving the plurality of interference patterns by a plurality of disjoint subsets of pixels, wherein a wavelength range of each narrow band wavelength filter falls within the broad wavelength spectrum of light of the point light source, and wherein wavelength ranges of respective narrow band wavelength filters are non-overlapping.

A third aspect of the present disclosure, discloses the use of an apparatus according to any of the embodiments of the first aspect, for performing in-line lens-free digital holography of an object, by receiving and recording, at the same moment in time, a plurality of interference patterns by a respective plurality of disjoint subsets of pixels.

According to preferred embodiments, the object is a biological object, such as for instance a cell, a virus or a tissue.

A fourth aspect of the present disclosure, discloses a computer program product suitable for deriving phase information of an object based on a plurality of interference patterns received and recorded at the same moment in time by the apparatus according to any of the embodiments of the first aspect, when run on a computer.

BRIEF DESCRIPTION OF THE DRAWINGS

The disclosure will be further elucidated by means of the following description and the appended figures.

FIG. 7 (a) to (d) is a schematic illustration of the simulation results supporting the effectiveness of aspects of the present disclosure.

FIG. 8 (a) shows a simulated snapshot image and FIG. 8 (b) a single wavelength reference, allowing an assessment of output resolution and image quality of methods according to aspects of the present disclosure.

DETAILED DESCRIPTION OF PREFERRED EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

Figure 1:
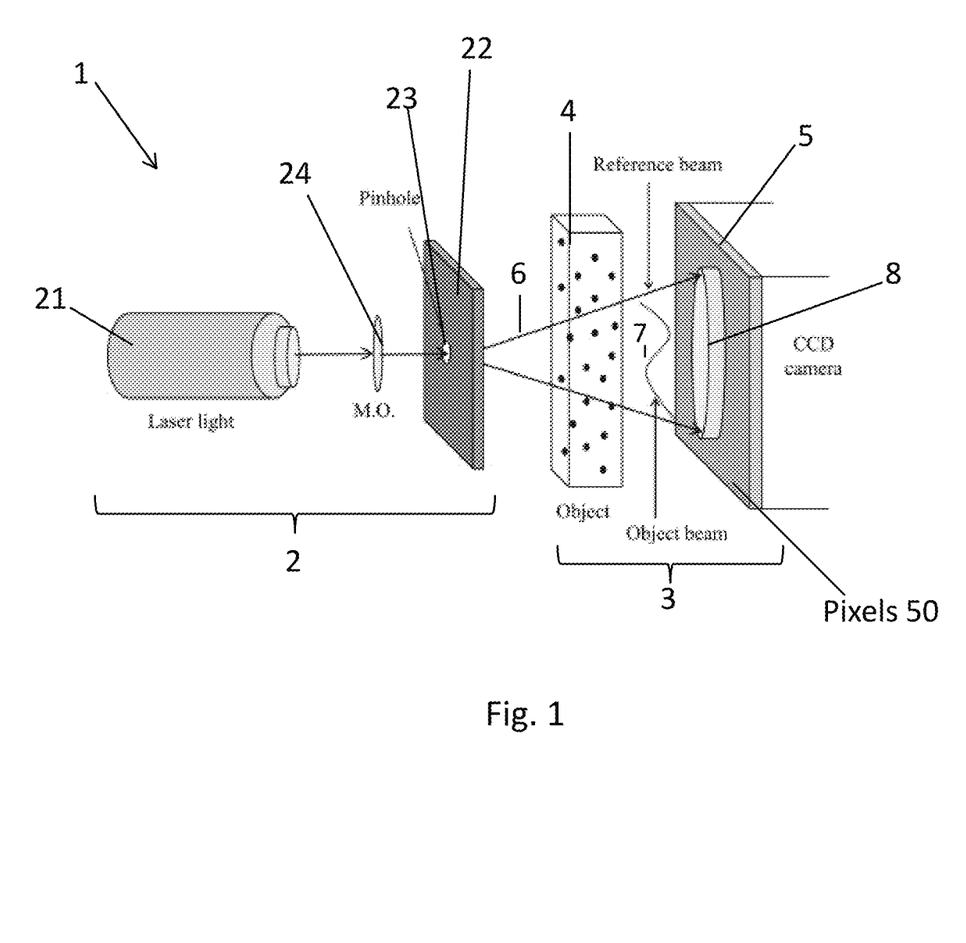
FIG. 1 shows a prior art setup of an in-line lens-free digital holography apparatus, on which the preamble of claim 1 is based.

FIG. 1 illustrates a typical state of the art holographic apparatus 1 for performing in-line lens free digital holography of an object, preferably a translucent or transparent object. This apparatus 1 comprises a single point light source 2, being a light source of the point source type, adapted for emitting coherent or essentially coherent light. The single light source may be constituted of different components, and may comprise a plate 22 with a pinhole 23 positioned in front of a light source 21 as for instance a laser or LED light source. Between the light source 21 and the plate or light blocking means 22, optical components 24 may be provided such as for instance one or more lenses. Note that embodiments of the present invention are anyhow called "lens-free" as this does only refer to the fact that no optical components as for instance lenses are present or used on the side of the plate or light blocking means 22 opposite to the side where the laser or LED light source is located. The apparatus or system further comprises an object space 3 suitable for locating the object 4 and positioned in close proximity of the point light source 2, for subjecting the object 4 to light waves 6 of the point light source 2. The system or apparatus further comprises a digital image sensing device 5 adapted and arranged for recording two-dimensional interference patterns 8 within the three-dimensional interference space. The three-dimensional interference space is resulting from the interference of light waves 6 directly originating from the point source 2 and object light waves 7. This object light waves 7 originate from scattering and/or reflection of light waves emitted from the point light source 2 by the object 4. The digital image sensing device 5 typically comprises a plurality of pixels 50. A problem with this state of the art in-line lens free digital holography setup, is that an inherent artifact of a twin image is created in the interference patterns 8, which are detected with the digital image sensing device 5.

According to aspects of the present invention, a similar holographic apparatus 1 is disclosed, wherein the digital image sensing device 5 is adapted for receiving and recording, at the same moment in time, a plurality of interference patterns 8 by a respective plurality of disjoint subsets of pixels. The plurality of interference patterns obtained as in embodiments of the present invention have been shown to be suitable for retrieving or deriving phase information of the three-dimensional interference space, especially phase information about the object. According to preferred embodiments the digital image sensing device further comprises a processing means adapted for deriving or retrieving the phase information based on, or at least on, the plurality of interference patterns 8 registered by the digital image sensing device 5.

Figure 2:
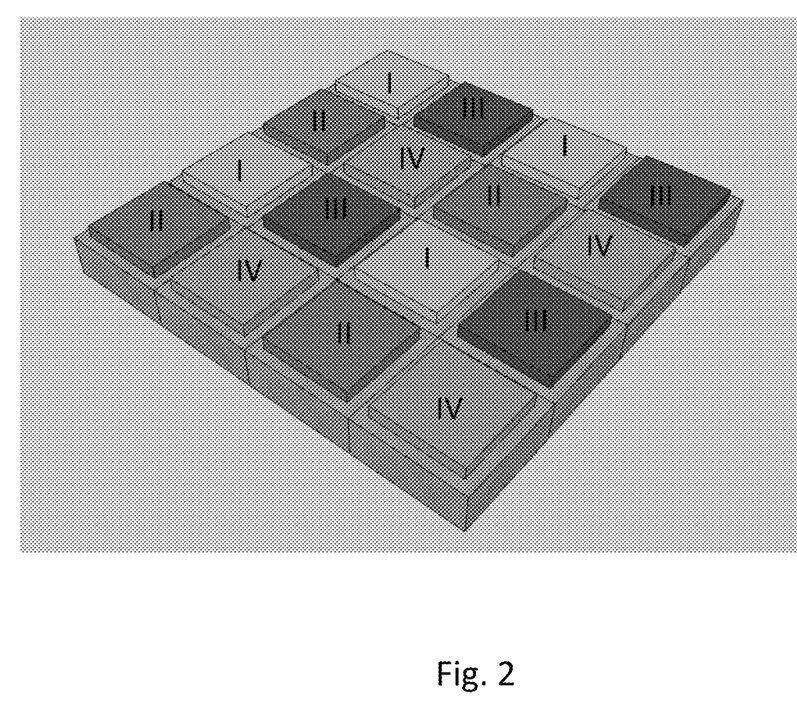
FIG. 2 is a perspective view of an embodiment according to the present disclosure.

FIG. 2 depicts an embodiment according to aspects of the present invention, wherein the digital image sensing device 5 comprises a plurality of pixels 50 which are arranged in a regular spaced matrix pattern. Preferably the pixels of each subset of pixels are homogeneously distributed over a main planar surface of the image sensing device 5. As pixels are preferably arranged in a regular matrix formation, the fact that the pixels of each subset of pixels are homogenously distributed over a main planar surface of the image sensing device, may imply that the pixels of each subset of pixels are spaced from each other at constant distances. The respective resulting grids, for each subset of pixels, are offset with respect of each other by constant distances.

For instance, in case the total amount of pixels 50 of the digital image sensing device 5 is divided in two subsets (I, II) of pixels which are equal in number, they can be distributed in a chess board formation. According to preferred embodiments, four subsets of pixels (I, II, III, IV) are formed which are equal in number of pixels, which are forming four-pixel squares. The four pixel positions of the four-pixel squares are represented by a pixel of each group of subset of pixels (I, II, III, IV) respectively. Such a four-pixel square formation may be repeated regularly and systematically along the main surface of the sensing device 5, for instance to thereby fill the complete main surface of the digital image sensing device 5.

According to preferred embodiments of the present invention, a variation in illumination wavelength is applied to acquire, in multiple holograms or interference patterns 8, slightly different information about the same object 4. This information is later recombined, for instance in an iterative phase retrieval algorithm, which is generally known to the skilled person, to suppress the twin image. In the state of the art, a multi-wavelength iterative phase retrieval method requires multiple holograms acquired with different illumination wavelengths. This is also the case in other multi-image correction methods. Aspects of the present invention are based on the idea of filtering the wavelengths only at the image sensing device or imager 5. This is after the moment that the photons of different wavelengths, originating from a broad wave-length spectrum light source, which is comprised in the point light source 2, have interfered with the object 4. This means that multiple photons with different wave lengths all interact with the object at the same time and this diffraction can be captured at a single moment, by means of a single digital image sensing device 5. According to preferred embodiments, a special designed image sensing device has been provided that can separate the different wave lengths and so the different interference patterns (or holograms). It is proposed to use multiple very narrow and preferably non-overlapping spectrum filters for different neighboring pixels of such a digital image sensing device 5. The filters can be pixel level integrated. This is depicted for instance in FIG. 2, wherein 4 by 4 pixels are disclosed of a digital image sensing device, wherein every 2 by 2 pixel sub array (four-pixel square) has four different narrowband filters (F1, F2, F3, F4) processed on top of its pixels. This imager can filter four different wave lengths and so four different hologram patterns from a single wideband coherent illumination 6 which interferes with the object light waves 7. These two by two subsets are repeated over the whole surface of the imager, creating a regular raster of pixels with individual wavelengths. This basically means that the size of the four recorded holograms (recorded different wavelengths W1, W2, W3, W4) is one fourth (½ in each dimension) of the size of the digital image sensing device 5. For example, the four by four image sensing device 5 in FIG.

1 is adapted for recording four holograms in a single shot: hologram 1 (2 by 2 pixels) at a wavelength W1 filtered out by filter F1, hologram 2 (2 by 2 pixels) at a wavelength W2 filtered out by filter F2, etc. A simple image interpolation technique can be used to up-sample the individual holograms H1 to H4 into full size (four times four) holograms H1' to H4'. These up-sampled holograms can then be used as an input for a multi wavelength iterative phase retrieval algorithm.

Figure 3:
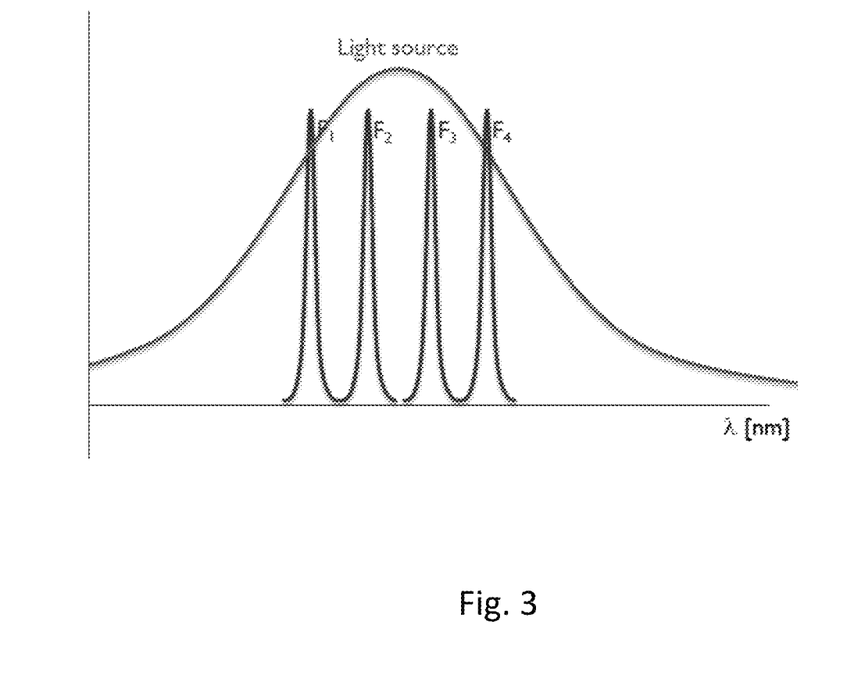
FIG. 3 is an illustration of the relative proportion and positioning of the broad band spectrum of the point light source and the narrow bands of the wavelength filters, according to a preferred embodiment of the present invention illustrated in FIG. 2.

The high-speed single shot lens free imaging system may comprise a wideband coherent light source, as for instance a LED or for instance super-continuum laser as a wide laser. FIG. 3 illustrates the spectral characteristics of the wideband coherent light source (for instance a LED or super-continuum laser) and the four corresponding narrowband filters F1 to F4 as described in relation to FIG. 2. Simulations and experiments have shown that there may be an approximately 30 to 40% degradation in final image resolution when comparing the 'snapshots' four-wavelength reconstruction results with results based on a full sized single image reconstruction scenario. However the multi wavelength approach according to preferred embodiments of the present invention can recover the phase information, which the state of the art single-image reconstruction cannot.

Figure 4:
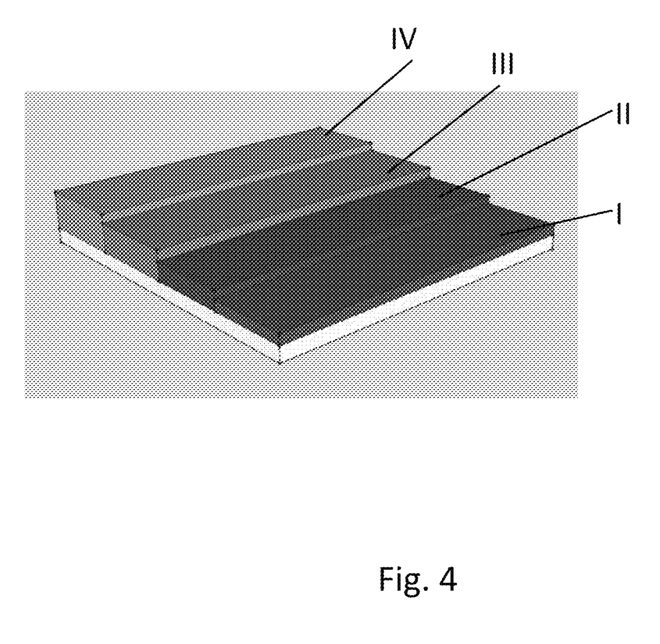
FIG. 4 is a perspective view of a further embodiment according to the present disclosure.

According to a further embodiment of the present invention, of the line-scanner type, the filters can be spread across the image sensor in a staircase/wedge pattern, for instance as depicted in FIG. 4. Each filter can hereby cover a row of pixels of the image sensing device. This 'wedge' architecture may be more suitable when there is a natural translation and movement in the object scene. Typical example is when objects are passed along a conveyer belt or roll along in between the imager with the filters on one side and the light source on the other side. In these embodiments the pixels of each disjoint subset of pixels of the digital image sensing device are arranged in rows of the regularly spaced matrix pattern. Each filter area corresponds to a different narrowband region. Each filter area captures the part of the hologram corresponding to the specific wavelength of the filter. By scanning the object of interest, each filter area will capture the complete hologram at a specific wavelength. Once a scan or scanning movement is completed, holograms of different wavelengths are then used in a multi wavelength phase retrieval algorithm. Note that unlike in the previous embodiment, all the captured holograms are of the same resolution as the imager in one dimension (the other dimension is of arbitrary length as this is determined by the scan direction and length). It is an advantage of this type of embodiments that one is able to achieve high-speed interference pattern recording by employing parallel multi wavelength imagers by exploiting the natural translation movement in such predetermined applications.

Figure 5:
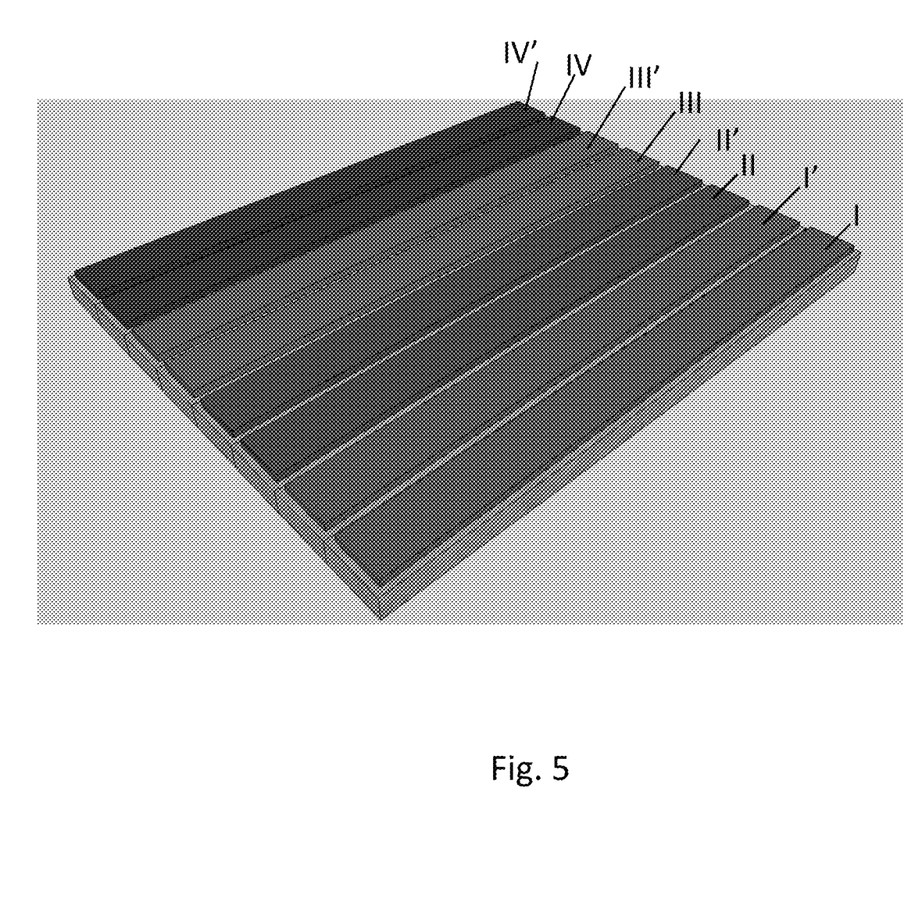
FIG. 5 is a perspective view of a still further embodiment according to the present disclosure.
Figure 6:
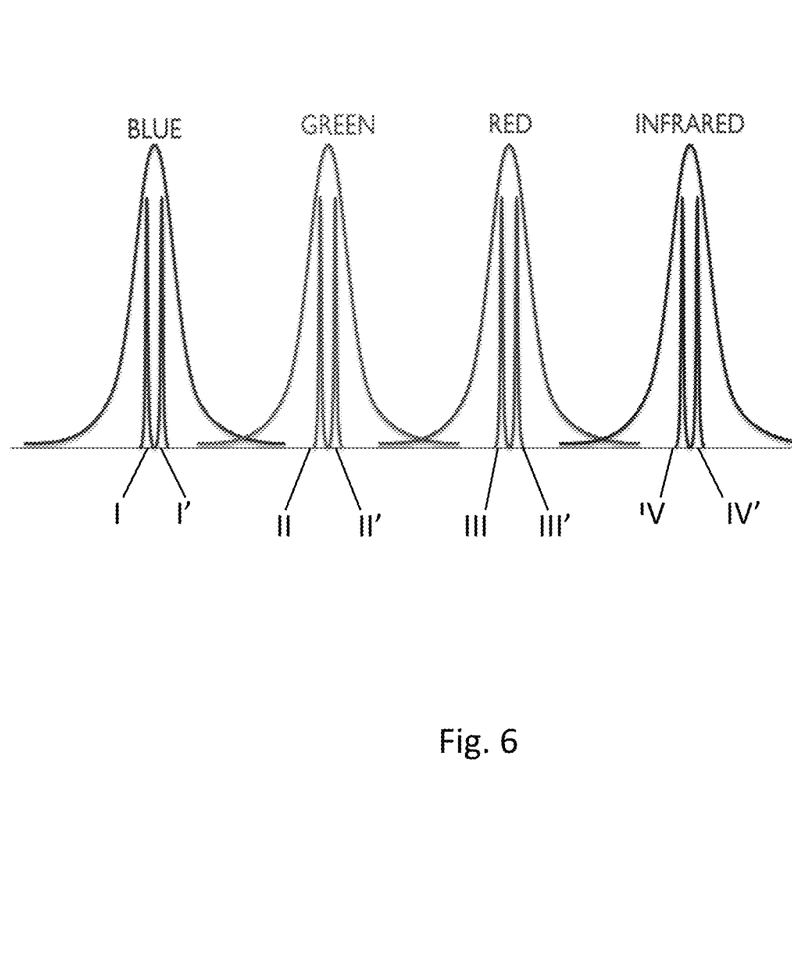
FIG. 6 is an illustration of the relative proportion and positioning of the broad band spectrum of the point light source and the narrow bands of the wavelength filters, according to a preferred embodiment of the present invention illustrated in FIG. 5.

In still another embodiment of the present invention, also of the line-scanner type, as depicted for instance in FIG. 5, the filters (I, I', II, II', III, III', IV, IV') are spread across the image sensor as parallel stripes. They can be processed in sets of filters (for instance sets of two filters) per color. For instance, four color images, corresponding to different color-categories, as for instance Red (R), Green (G), Blue (B), InfraRed (IR), can be generated while line-scanning (resulting from a relative translational movement between apparatus and object). Indeed, four sets of for instance two filters are provided (I, I'), (II, II'), (III, III'), (IV, IV'), the filters of each set belonging to the same color category. Images recorded with filters of the same color category then allow reduction or removal of the twin-image effect for image of the respective color category. This architecture realizes full color or multicolor lens free imaging systems. Hereby the colors and thus respective filters can be chosen specifically based on a predetermined application requirement. In this embodiment, two wavelengths are being used per color (to be able to use the iterative phase retrieval methods per color) and a total of four color categories, namely the blue, green, red and infrared color categories, enabling full color/four color lens free line scanning. FIG. 6 illustrates the spectral characteristics of the full color (RGBI) line scanner described in relation with FIG. 5, comprising two narrowband spectral filters (I, I'), (II, II'), (III, III'), (IV, IV') per color (R,G,B,IR).

A skilled person would recognize that embodiments of the present invention provide several advantages. A single shot recording of multiple diffraction patterns (holograms) is possible, which enables iterative phase retrieval algorithms to be performed without incurring the previously described issues related to the retrieval of multiple diffraction patterns at different instances of time (time domain, vibration, object rotation, etc.), or at different locations (spatial domain; object too far). Embodiments of aspects of the present invention allow high-speed lens free imaging. The acquisition speed equals the imager frame rate. Moreover, filter or delay structure can be chosen based on application requirements. For instance the filter wave lengths can be chosen based on application requirements. The point light source can be cheap, it can for instance be a simple led light source, and does not necessarily have to be a laser or a plurality of lasers. Also, the use of a single source is sufficient for performing methods according to aspects of the present invention. It has also been found that relatively simple image reconstruction algorithms can be used, because of the relatively simple setup.

Simulations have been made to illustrate the concept of aspects of the present disclosure. A simulation was first made of the outcome of the image sensor with the per-pixel filters on top in "snapshot" approach; i.e. wherein a plurality of interference patterns (here four) are received and recorded at the same moment in time, by a respective plurality of disjoint subsets of pixels. The simulation simulated the virtual result when using an image sensing device comprising for each of the four disjoint subsets of pixels, a respective narrow band wavelength filter (of four filters) positioned above each of the pixels of the disjoint subset of pixels, the wavelength range of each narrow band wavelength filter falling within the broad wavelength spectrum of the point light source, the wavelength ranges of the narrow band wavelength filters being non-overlapping. The simulated results are then compared with a reference image based on a non-iterative approach, being a single-wavelength image reconstruction.

Under normal operating conditions of the snapshot approach, all four wavelengths are illuminating the object (and the sensor) at the same time. The filters on top of the sensor select only one narrow wavelength range for each pixel, which can be considered to record only one wavelength (or narrow wavelength range). To simulate this, a traditional sequential recording was performed, whereby the full sensor was illuminated sequentially with the four wavelengths hence resulting in four full resolution recordings (FIG. 7(a)).

Figure 7:
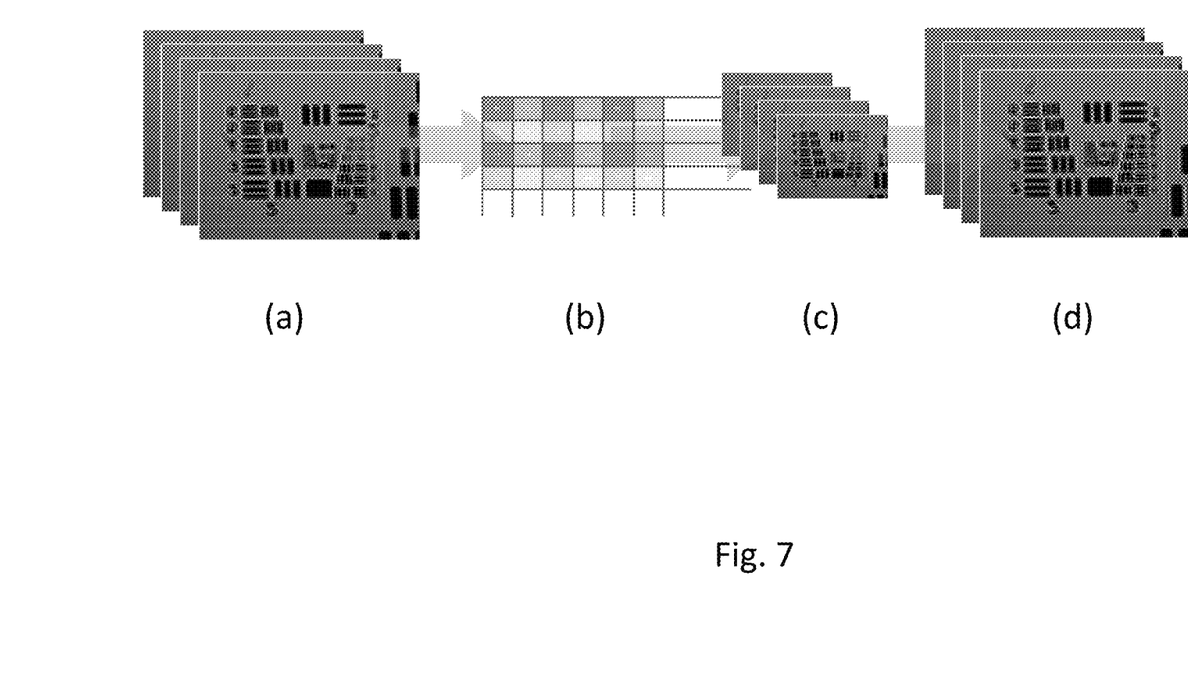

Then, the behavior of the snapshot sensor was simulated by subsampling these full resolution images the way the wavelength filters are to be organized on the sensor (see e.g. FIG. 7 (b)). As a result, four low(er) resolution images are generated (FIG. 7(c)). The processed snapshot sensor would acquire one image at a time. It is straight forward to then separate this single image into a (similar) subset of four low(er) resolution images.

Figure 8:
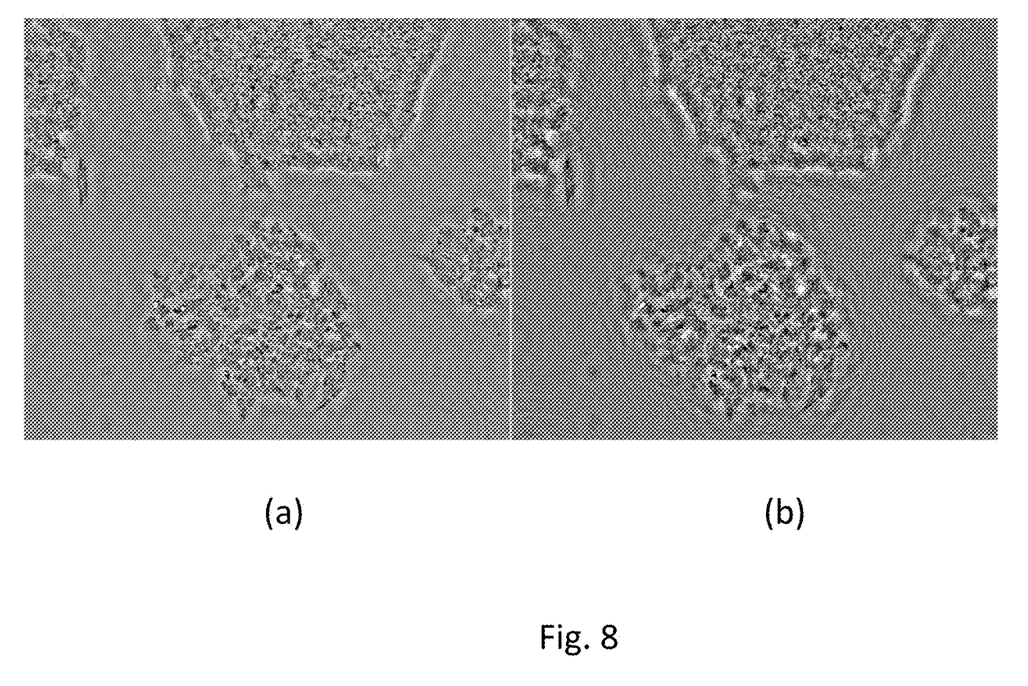

To compare the outcome of this approach, an image interpolation step to go back to the original resolution of the input images was performed (FIG. 7(d)). This is to be able to compare the obtained quality and resolution of the snapshot approach versus the sequential approach. A normal multi-wavelength iterative reconstruction process was done. A comparison of the results is depicted in FIGS. 8(a) and (b). Indeed, if high speed imaging is a strict requirement, then the resulting quality and resolution should best be compared with a single-wavelength (non-iterative) reconstruction.

It is clear that the resulting image quality is much better with the (simulated) snapshot approach (FIG. 8(a)) when compared to the non-iterative approach (FIG. 8(b)). This is at least due to the inherent twin-image distortion of the single wavelength reconstruction. With the (simulated) snapshot approach, an iterative reconstruction is still possible, which clearly results in a suppression of the inherent twin-image distortion.

The invention claimed is:

1. An apparatus for performing in-line lens-free digital holography of an object, comprising:
   a point light source adapted for emitting coherent light; and
   an image sensing device adapted and arranged for recording interference patterns resulting from interference from light waves directly originating from the point light source and object light waves,
   wherein the object light waves originate from light waves from the point light source that are scattered or reflected by the object,
   wherein the image sensing device comprises a plurality of pixels apportioned between disjoint subsets of pixels,
   wherein the point light source comprises a broad wavelength spectrum light source and a pinhole structure, the broad wavelength spectrum light source being arranged to emit light towards the pinhole structure,
   wherein the image sensing device comprises, for each of the disjoint subsets of pixels, a respective narrow band wavelength filter positioned above each pixel in the disjoint subset of pixels,
   wherein a wavelength range of each narrow band wavelength filter falls within a broad wavelength spectrum of the point light source,
   wherein the wavelength ranges of the narrow band wavelength filters are non-overlapping, and
   wherein the image sensing device is adapted for receiving and recording, while subjecting the object to light waves emitted from the point light source, a plurality of interference patterns by a respective plurality of the disjoint subsets of pixels.

2. The apparatus according to claim 1, further comprising a processing means adapted for deriving phase information based on at least the plurality of interference patterns.

3. The apparatus according to claim 1, wherein the plurality of pixels is arranged in a regularly spaced matrix pattern.

4. The apparatus according to claim 3, wherein the pixels of each disjoint subset of pixels are arranged in rows of the regularly spaced matrix pattern.

5. The apparatus according to claim 1, wherein the pixels of each disjoint subset of pixels are spaced from each other at constant distances, and wherein respective resulting grids are offset with respect to each other by constant distances.

6. The apparatus according to claim 1, wherein the pixels of each disjoint subset of pixels are homogeneously distributed over a main planar surface of the image sensing device.

7. The apparatus according to claim 1, wherein the broad wavelength spectrum light source comprises a white laser device or an LED device.

8. The apparatus according to claim 1, wherein the wavelength range of each narrow band wavelength filter is smaller than N nm, and wherein the broad wavelength spectrum of the point light source has a wavelength range larger than N×M nm, wherein M is a number of narrow band wavelength filters of the apparatus.

9. A method for performing in-line lens-free digital holography of an object, comprising:
   emitting coherent light from a point light source;
   locating the object in an object space positioned in close proximity to the point light source, and subjecting the object to light waves of the point light source;
   receiving and recording, by an image sensing device comprising a plurality of pixels apportioned between disjoint subsets of pixels, interference patterns resulting from interference from light waves directly originating from the point light source and object light waves, wherein the object light waves originate from light waves from the point light source that are scattered or reflected by the object; and
   filtering, with respective narrow band wavelength filters, the incoming light waves directly originating from the point light source and the object light waves,
   wherein receiving and recording interference patterns comprises receiving and recording, while subjecting the object to light waves emitted from the point light source, a plurality of interference patterns by a respective plurality of the disjoint subsets of pixels,
   wherein emitting coherent light from the point light source comprises emitting a broad wavelength spectrum of light with the point light source,
   wherein the respective narrow band wavelength filters filter a similar wavelength range for each of the pixels belonging to a common disjoint subset of pixels for each disjoint subset of pixels,
   wherein a wavelength range of each respective narrow band wavelength filter falls within the broad wavelength spectrum of light emitted by the point light source,
   and wherein the wavelength ranges of the respective narrow band wavelength filters are non-overlapping.

10. The method according to claim 9, further comprising deriving phase information of the object by performing an iterative phase retrieval algorithm using the interference patterns, performed on a processing means.

11. The method according to claim 9, wherein the plurality of pixels is arranged in a regularly spaced matrix pattern.

12. The method according to claim 11, wherein the pixels of each disjoint subset of pixels are arranged in rows of the regularly spaced matrix pattern.

13. The method according to claim 9, wherein the pixels of each disjoint subset of pixels are homogeneously distributed over a main planar surface of the image sensing device.

14. A non-transitory, computer-readable medium with instructions executable by a processor stored thereon, wherein when the processor executes the instructions, the processor performs to derive phase information about an object based on a plurality of interference patterns received and recorded, at the same moment in time, by an apparatus comprising:

a point light source adapted for emitting coherent light; and
an image sensing device adapted and arranged for recording interference patterns resulting from interference from light waves directly originating from the point light source and object light waves,
wherein the object light waves originate from light waves from the point light source that are scattered or reflected by the object,
wherein the image sensing device comprises a plurality of pixels apportioned between disjoint subsets of pixels,
wherein the point light source comprises a broad wavelength spectrum light source and a pinhole structure, the broad wavelength spectrum light source being arranged to emit light towards the pinhole structure,
wherein the image sensing device comprises, for each of the disjoint subsets of pixels, a respective narrow band wavelength filter positioned above each pixel in the disjoint subset of pixels,
wherein a wavelength range of each narrow band wavelength filter falls within a broad wavelength spectrum of the point light source,
wherein the wavelength ranges of the narrow band wavelength filters are non-overlapping, and
wherein the image sensing device is adapted for receiving and recording, while subjecting the object to light waves emitted from the point light source, the plurality of interference patterns by a respective plurality of the disjoint subsets of pixels.

15. The non-transitory, computer-readable medium of claim 14, wherein the plurality of pixels is arranged in a regularly spaced matrix pattern.

16. The non-transitory, computer-readable medium according to claim 15, wherein the pixels of each disjoint subset of pixels are arranged in rows of the regularly spaced matrix pattern.

17. The non-transitory, computer-readable medium according to claim 14, wherein the pixels of each disjoint subset of pixels are spaced from each other at constant distances, and wherein respective resulting grids are offset with respect to each other by constant distances.

18. The non-transitory, computer-readable medium according to claim 14, wherein the pixels of each disjoint subset of pixels are homogeneously distributed over a main planar surface of the image sensing device.

19. The non-transitory, computer-readable medium according to claim 14, wherein the broad wavelength spectrum light source comprises a white laser device or an LED device.

20. The non-transitory, computer-readable medium according to claim 14, wherein the wavelength range of each narrow band wavelength filter is smaller than N nm, and wherein the broad wavelength spectrum of the point light source has a wavelength range larger than N×M nm, wherein M is a number of narrow band wavelength filters of the apparatus.

* * * * *